United States Patent [19]

Gradel et al.

[11] Patent Number: 4,663,112
[45] Date of Patent: May 5, 1987

[54] METHOD FOR DETERMINING THE CONTENTS OF A FUEL ROD

[75] Inventors: Gerhard Gradel, Eckersdorf; Peter Wahode, Neunkirchen; Wolfgang Dörr, Herzogenaurach, all of Fed. Rep. of Germany

[73] Assignee: Kraftwerk Union Aktiengesellschaft, Mülheim, Fed. Rep. of Germany

[21] Appl. No.: 589,513

[22] Filed: Mar. 14, 1984

[30] Foreign Application Priority Data

Mar. 24, 1983 [DE] Fed. Rep. of Germany ....... 3310755

[51] Int. Cl.$^4$ .............................................. G21C 17/00
[52] U.S. Cl. .................................... 376/245; 376/257
[58] Field of Search ................ 376/245, 257; 324/207, 324/208; 340/870.36; 336/30.45

[56] References Cited

U.S. PATENT DOCUMENTS

| | | |
|---|---|---|
| 3,787,761 | 1/1974 | Grossman et al. .................. 376/257 |
| 4,229,654 | 10/1980 | Arya et al. ........................... 376/257 |
| 4,347,622 | 8/1982 | Bernatowicz et al. ............. 376/257 |

FOREIGN PATENT DOCUMENTS

| | | |
|---|---|---|
| 2643664 | 3/1978 | Fed. Rep. of Germany . |
| 2758051 | 6/1978 | Fed. Rep. of Germany . |
| 2433181 | 3/1980 | France . |
| 2073429 | 10/1981 | United Kingdom . |

Primary Examiner—Salvatore Cangialosi
Attorney, Agent, or Firm—Herbert L. Lerner; Laurence A. Greenberg

[57] ABSTRACT

Method for determining the contents of a fuel rod within a testing range extending in the longitudinal direction of the fuel rod, characterized by the features that
(a) the position of a test coil concentrically surrounding the fuel rod is changed from the beginning to the end of the testing range, and
(b) in the process, the impedance of the test coil is measured as a function of its position,
(c) the test coil is fed with an a-c voltage,
(d) the frequency of which is so low that the measurement value in the region of a fuel pellet of pure uranium dioxide is clearly distinguished from that which is measured in the region of a doped fuel pellet.

3 Claims, 2 Drawing Figures

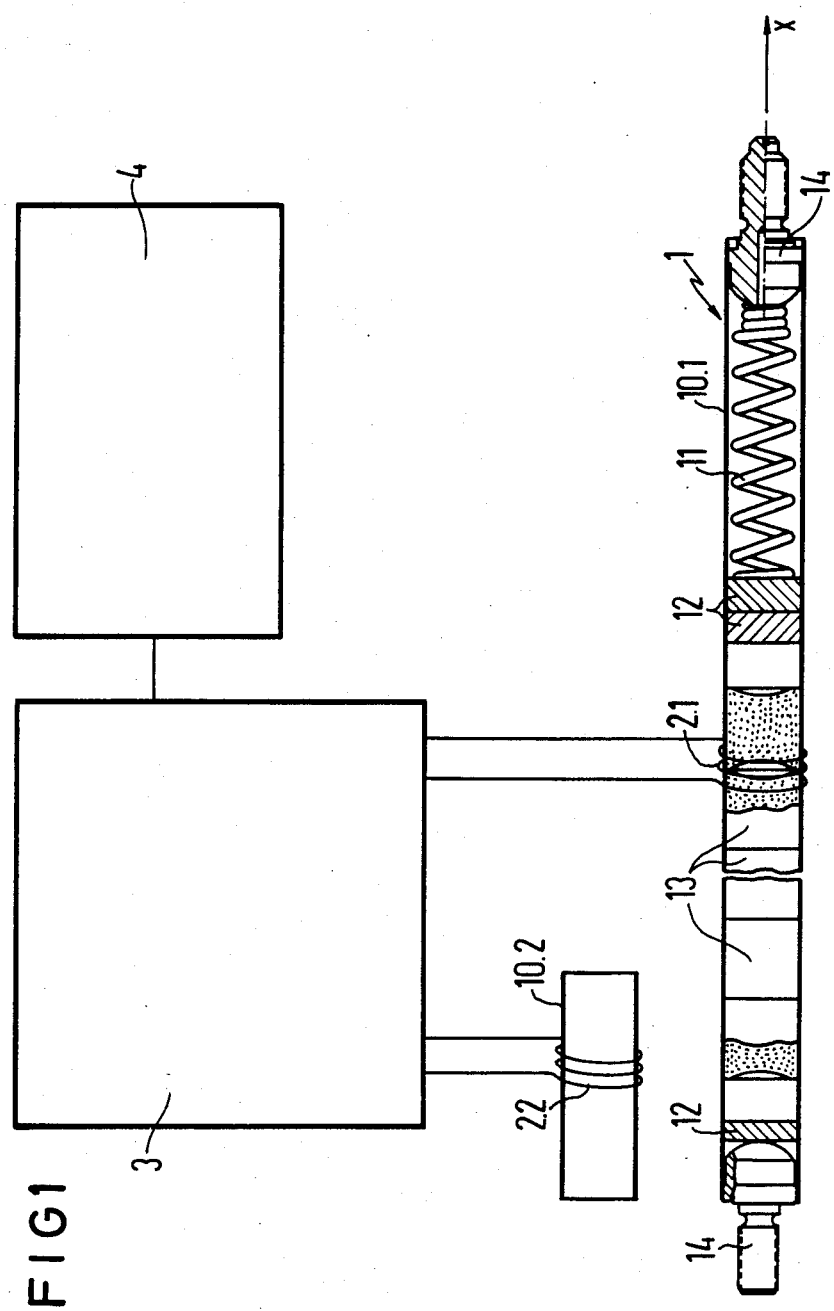

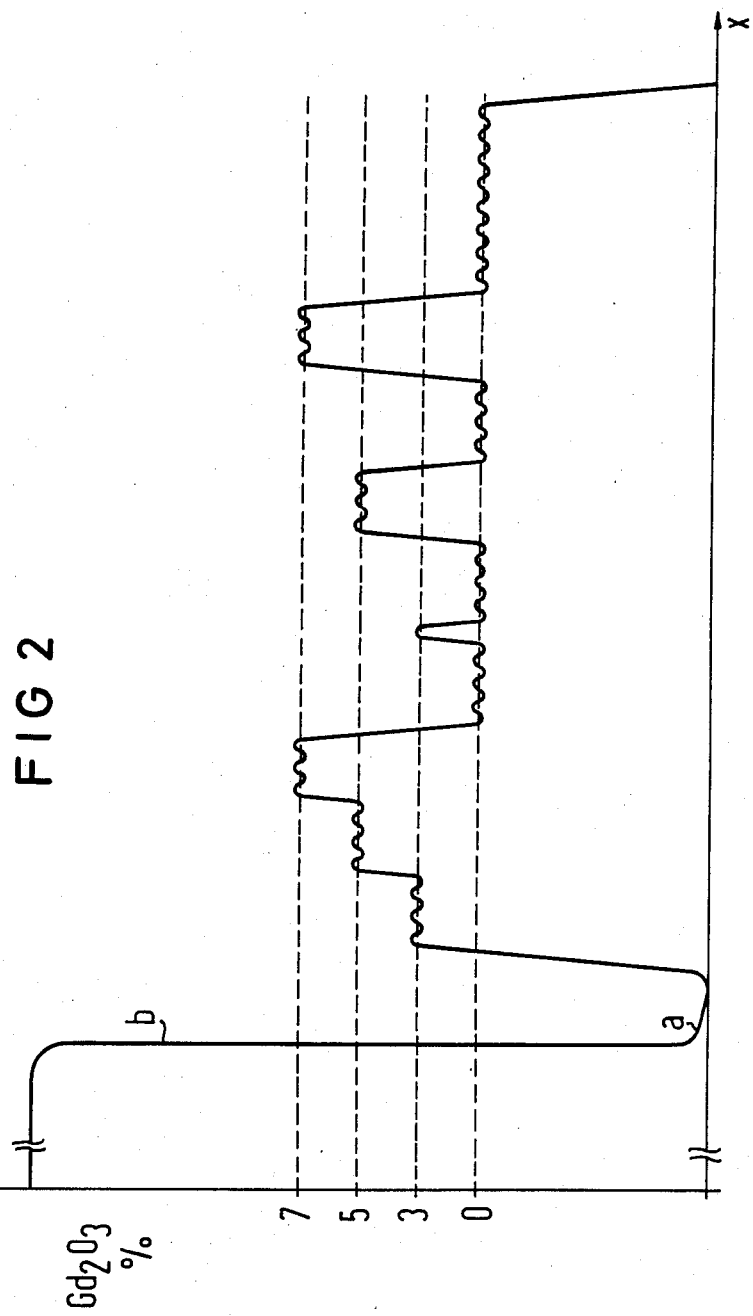

METHOD FOR DETERMINING THE CONTENTS OF A FUEL ROD

BACKGROUND OF THE INVENTION

1. Field of the Invention

The invention relates to a method for determining the contents of a fuel rod within a test range extending along the length of the fuel rod. The objective in particular is to distinguish fuel pellets of pure uranium dioxide from those which are doped with oxides of rare earths, for instance, with gadolinium oxide, $Gd_2O_3$.

2. Description of the Prior Art

Heretofore, for this purpose, the closed fuel rod has been irradiated with a neutron source and subsequently, the secondary radiation of the fuel rod was recorded over its length. This secondary radiation of differently doped fuel pellets can be distinguished from the radiation of pure $UO_2$ in the fuel rod. However, this so-called "rod scanning" requires considerable equipment in the form of a large number of measuring devices and radiation protection measures which represent a substantial investment.

SUMMARY OF THE INVENTION

An object of the invention is to provide a method for distinguishing doped fuel pellets from those of pure $UO_2$ in fuel rods with materially less investment cost than the method heretofore used, and in particular without the requirement for the radiation protection measures previously needed.

With the foregoing and other objects in view, there is provided in accordance with the invention a method for determining the contents of a fuel rod containing fuel pellets of pure uranium dioxide and doped fuel pellets within a test range extending along the length of the fuel rod which comprises concentrically surrounding the fuel rod with a test coil and moving the test coil from the beginning to the end of the test range, measuring the impedance of the test core as a function of its position during movement, and feeding the test coil an a-c voltage with a frequency sufficiently low to produce a measurement value in the region of a fuel pellet of pure uranium dioxide which clearly distinguishes from a measurement value in the region of a doped fuel pellet.

Other features which are considered as characteristic for the invention are set forth in the appended claims.

Although the invention is illustrated and described herein as embodied in a method for determining the contents of a fuel rod, it is nevertheless not intended to be limited to the details shown, since various modifications may be made therein without departing from the spirit of the invention and within the scope and range of equivalents of the claims.

BRIEF DESCRIPTION OF THE DRAWINGS

The invention, however, together with additional objects and advantages thereof will be best understood from the following description when read in connection with the accompanying drawings, in which:

FIG. 1 diagrammatically illustrates a measuring setup for determining the contents of a fuel rod in accordance with the invention. A fuel rod which has a cladding tube enclosing pellets of pure $UO_2$ and doped fuel pellets as well as structural material is moved through a test coil surrounding the fuel rod. The test coil is fed a-c voltage with a low frequency to produce measurement values resulting from the impedance of the test coil to distinguish the pure $UO_2$ pellets from the doped fuel pellets. A recorder, controlled by an eddy current test equipment, records the measured impedance. Also connected to the eddy current test equipment is an additional comparison coil which surrounds an empty comparison tube section.

FIG. 2 shows a fuel rod profile taken along the length of the fuel rod. The percent $Gd_2O_3$ is indicated as well as the location of structural material in the fuel rod.

DETAILED DESCRIPTION OF THE INVENTION

The conductivity differences between pure and doped material in a fuel rod are evaluated by means of an eddy current measuring method. To this end, the impedance of a test coil surrounding the fuel rod is measured. The frequency of the a-c voltage feeding this test coil method is chosen so low that conductivity differences due to different doping of the fuel pellets within the tube can be measured.

The position of a test coil concentrically surrounding the fuel rod is changed from the beginning to the end of the testing range. In the process, the impedance of the test coil is measured as a function of its position. The test coil is fed with an a-c voltage, the frequency of which is so low that the measured value in the region of a fuel pellet of pure uranium dioxide differs distinctly from that which is measured in the region of the doped fuel pellet.

The method according to the invention is based on the finding that the conductivity of the fuel pellets increases steeply even with slight doping and small differences in the conductivity can be measured with a magnetic field penetrating an electrically conducting tube. At a suitably low frequency, sufficiently large impedance differences occur at the test coil.

Preferably, the measured values are recorded by a recorder as a function of the position of the test coil. For this purpose, the measured values can be digitalized in a transient recorder and stored in this form and optionally evaluated simultaneously or later by a computer. In this manner, fast changes of the measured value, for instance at the pellet boundaries, which are not displayed by a measuring recorder which is too sluggish, become visible. This procedure makes it possible to select a value sufficiently high for practical requirements (for instance 10 cm/sec) for the passage velocity of the fuel rod through the test coil.

As a result of measuring the impedance of a test coil surrounding the fuel rod in accordance with the invention, a profile typical of the contents of the fuel rod is produced. This allows not only the determination of the doping concentration of the fuel pellets and thereby a distinction of pellets with different dopings, even if the differences between pellets is only 1%. In addition, metallic occlusions in the pellet, undesirable spacings between adjacent pellets and their skewed position can be determined, as well as the location of structural material, for instance, of springs or aluminum oxide pellets. Finally, the length of the pellet column can also be measured in this manner.

Observing the proper radiation protection measures, the invention can also be used, of course, for measuring fuel rods which have been irradiated. The invention utilizes the well-known eddy current method and the test equipment and apparatus known for carrying it out. In this method, the change of the impedance of a test coil is evaluated if a test piece is introduced into the latter. The change in impedance depends here on quality features of the test piece such as material faults, dimensional deviations, etc. Here, however, the test piece was always of metal throughout. With the invention, however, ceramic or semiconducting material is measured which is surrounded by an electrically conducting metal tube.

As in the known cases, the absolute value of the impedance can be measured and indicated with the invention; higher sensitivity, however, is obtained with a reference value method, in which the difference between the measured value of the test piece and the measured value of a comparison object is evaluated. The comparison object is preferably a tube which is surrounded by a comparison coil and is advantageously filled with a fuel pellet, the data of the tube and the fuel pellet being the same as the reference data of the fuel rods to be measured. However, the comparison coil can also surround the fuel rod to be measured physically next to the test coil.

Preferably, the test coil or an additional auxiliary coil is subjected to at least one additional a-c voltage of higher frequency and the impedance so determined is measured and evaluated. In this manner, other properties of the test piece such as, for instance, thickness, eccentricity and homogeneity of the tube wall of the fuel rod can be measured at the same time by appropriate choice of the frequencies.

The invention is particularly well suited for an automated test in which the measured profile of the test pieces is compared with the desired profile of a good fuel rod and from the result of this comparison, a switch setting for sorting the test pieces is controlled.

An embodiment example of the invention will be explained in greater detail with reference to the drawings.

In the measuring arrangement of FIG. 1 is shown a fuel rod generally designated with 1 and its cladding tube 10.1. A spring 11, two pellets 12 of aluminum oxide, 36 fuel pellets 13 with different doping and a further pellet 12 of aluminum oxide are arranged between two closures 14 in the cladding tube 10.1.

This fuel rod is moved through a test coil 2.1 in the direction of the arrow x, the measured impedance being recorded according to FIG. 2 by a recorder 4. Recorder 4 is controlled by an eddy current test equipment 3 to which an additional comparison coil 2.2 is connected which surrounds an empty comparison tube section 10.2. The comparison coil and the test coil are fed from the eddy current test equipment with an a-c voltage of correspondingly low frequency, and the impedance difference between the auxiliary coil 2.2 and the test coil 2.1 is measured and, after suitable amplification, is recorded by the recorder 4 over the length x of the fuel rod.

In FIG. 2 can clearly be seen the individual fuel pellets since they meet at the end faces not over the full areas but only over a circular ring. Each pellet is therefore imaged by a half-wave. The height level of these half-waves is in addition a measure for the doping, in this case for the $Gd_2O_3$ content in percent, of a fuel pellet which consists otherwise of $UO_2$. With this profile therefore one can without problem distinguish pure $UO_2$ pellets ($Gd_2O_3$ content=0%) from doped pellets; with suitable calibration, the degree of doping can even be measured. The profile indicates furthermore the location of structural material, where the branch a images the two aluminum oxide pellets 12 and branch b, the spring 11.

With the invention, the frequency of the a-c voltage at the test coil is below 10 kHz; in the known eddy current measuring methods, on the other hand, it is usually above 50 kHz. With a rod diameter of 12.5 mm and a wall thickness of 0.98 mm of the cladding tube, a frequency between 6.6 and 7.5 kHz has primarily been found to be particularly advantageous. With a thinner rod diameter of 9.7 mm and a wall thickness of 0.7 mm, 9 to 9.5 kHz have been used. The air gap between the individual pellets and the cladding tube is about 190 μm.

The foregoing is a description corresponding, in substance, to German application P 33 10 755.6, dated Mar. 24, 1983, international priority of which is being clamped for the instant application, and which is hereby made part of this application. Any material discrepancies between the foregoing specification and the specification of the aforementioned corresponding German application are to be resolved in favor of the later.

There is claimed:

1. Method for determining the contents of a fuel rod containing fuel pellets of pure uranium dioxide and doped fuel pellets within a test range extending along the length of the fuel rod which comprises concentrically surrounding the fuel rod with a test coil and moving the test coil from the beginning to the end of the test range, measuring the impedance of the test core as a function of its position during movement, and feeding the test coil an a-c voltage with a frequency below 10 kHz to produce a measurement value in the region of a fuel pellet of pure uranium dioxide which clearly distinguishes from a measurement value in the region of a doped fuel pellet.

2. Method according to claim 1, wherein the measured values are recorded by a recorder as a function of the position of the test coil within the test range extending along the length of the fuel rod in the form of a measurement profile.

3. Method according to claim 2, wherein the measurement profile of the fuel rod to be tested is compared with a desired profile of a good fuel rod and, wherein as a result of this comparison, a switch is set for sorting the fuel rods subsequent to the measurement to separate fuel rods not having desirable characteristics.

* * * * *